(12) United States Patent
Sperschneider

(10) Patent No.: US 6,185,273 B1
(45) Date of Patent: Feb. 6, 2001

(54) PROCESS AND CIRCUIT ARRANGEMENT FOR TESTING SOLDER JOINTS

(75) Inventor: Eckhard Sperschneider, Neubiberg (DE)

(73) Assignee: Macrotron Process Technologies GmbH (DE)

( * ) Notice: Under 35 U.S.C. 154(b), the term of this patent shall be extended for 0 days.

(21) Appl. No.: 09/068,295

(22) PCT Filed: Nov. 6, 1996

(86) PCT No.: PCT/EP96/04853

§ 371 Date: Oct. 26, 1998

§ 102(e) Date: Oct. 26, 1998

(87) PCT Pub. No.: WO97/17605

PCT Pub. Date: May 15, 1997

(30) Foreign Application Priority Data

Nov. 6, 1995 (DE) .............................. 195 41 322

(51) Int. Cl.[7] .................................. G01N 23/18
(52) U.S. Cl. ................................. 378/58; 378/62
(58) Field of Search ....................... 378/4, 22, 57, 378/58, 23, 24, 25, 51, 62, 207, 63

(56) References Cited

U.S. PATENT DOCUMENTS

| | | | |
|---|---|---|---|
| 4,809,308 | * | 2/1989 | Adams et al. ...................... 378/58 X |
| 4,852,131 | * | 7/1989 | Armistead ................................ 378/4 |
| 5,291,535 | | 3/1994 | Baker et al. ........................... 378/22 |
| 5,687,209 | * | 11/1997 | Adams ................................... 378/22 |
| 5,754,621 | * | 5/1998 | Suzuki et al. .......................... 378/57 |

FOREIGN PATENT DOCUMENTS 0 236 001 B1   8/1991   (EP) .............................. G01N/23/18

* cited by examiner

Primary Examiner—David P. Porta
(74) Attorney, Agent, or Firm—Fish & Richardson P.C.

(57) ABSTRACT

The invention concerns a process and circuit arrangement for testing solder joints, preferably on printed circuit boards, whereby the quality of the solder joints is examined for defects using X-rays and qualitative information on the individual solder joints is obtained. According to the invention, the qualitative and/or the measured values of the individual solder joints that characterize the measured physical parameters of the tested solder joints, are used to control the manufacture of further solder joints in the production process in which solder joints are tested.

10 Claims, 12 Drawing Sheets

Repair

PCB No.: 4711
Use No.: 0

◇ Top    ◇ Bottom

Defect list:

| | | | | |
|---|---|---|---|---|
| D400 | 1 | E | 65 Solder link | solder paste |
| D400 | 10 | E | 65 SMD missing | populator |
| D400 | 13 | E | 65 Wrong SMD | populator |
| O728 | 1 | S | 65 Solder bridge | solder paste |
| R726 | 2 | S | 33 Wet. Gullwing | soldering defect |
| R705 | 1 | S | 35 Wet.square.SMD | soldering defect |
| C705 | 2 | S | 36 SMD misplaced | populator |

Defect code: 69 ▼

| Next | Back | Next component |
|---|---|---|
| True defect | Pseudo defect | New defect |
| S/A done | S/A abort | Close |

Subassemblies Information

| Project | 108005 |
| --- | --- |
| Memory allocated | 500000 |
| Boards in memory | 22 |
| Memory per board | 17824 |

| Class | DIS | PTH | SOT | IC |
| --- | --- | --- | --- | --- |
| Measured values | 4 | 0 | 4 | 7 |
| Components | 34 | 0 | 6 | 11 |
| Solder joints | 70 | 0 | 18 | 268 |

[ OK ]  [ Help ]

FIG. 13

Limit value Configuration

Measured value
- ToeBoardDelta
- FilletSolder
- MeasuredFilletWidth
- OffPosSlope
- HeelPadDelta
- PadBoardDelta

DIS  PTH  SOT  IC

Upper warning limit        150

Lower warning limit         40

Minimum 35    Maximum 180

[ End ]  [ Accept ]  [ Store ]  [ Reset ]  [ Help ]

FIG. 14

PROCESS AND CIRCUIT ARRANGEMENT FOR TESTING SOLDER JOINTS

The invention relates to a process and a circuit arrangement for testing solder joints.

The quality of solder joints on printed circuit boards can be checked for defects by means of X-rays. In the process, solder-joint-specific quality information is formed, either the information "solder joint defect-free" or the information "solder joint defective" being formed for each solder joint. This information is printed out with reference to printed circuit boards, this print-out, together with the associated printed circuit board, being supplied to a repair workstation. There, the printed circuit boards which have at least one solder joint for which the information "solder joint defective" was formed is subjected to subsequent treatment, the allegedly defective solder joint being checked visually. If the result is that the solder joint is actually defective, the contact point having the original defective solder joint is re-soldered. A test is then carried out again to see whether this solder joint is now defect-free. These operations are noted in a report which, if necessary, is available for statistical evaluation.

EP 0 236 001 B1 has already disclosed a process and a device for measuring structural properties of selected regions of a manufactured printed circuit board having solder joints provided thereon. The device has an X-ray device for generating an X-ray beam, an imaging device for registering the X-rays transmitted through the printed circuit board in order to generate a corresponding electronic image, a processing device for converting the electronic image into an image encoded in accordance with a grey scale, and a computing device which carries out measurements on the image that has been encoded in accordance with a grey scale on the basis of measuring algorithms which are selected from a data library and which relate to predefinable electronic standard components and arrangements and to specific types of solder-joint defect that are associated with these (including "solder ball", "excess solder", "cold solder joint"). The computing device also generates an output signal which corresponds to a change in the measurements of the image encoded in accordance with a grey scale from predetermined measuring standards which, for their part, correspond to desired structural properties which are contained in the library. The output signal may also contain measurement data for the process control of printed circuits produced in the future. However, these measurement data are not used in the continuous production process in which the properties of the printed circuit boards are measured.

Processes for testing solder joints are also known from U.S. Pat. No. 5,291,535, from Soron, E.: "X-Ray Systems keep Pace with SMT", in Test & Measurement World incorp. Electronic Test 11 (1991) February 15, No. 3, San Francisco, Calif., US, pages 21/22 and from Driels, M. R. and Nolan, D. J.: "Automatic Defect Classification of Printed Wiring Board Solder Joints", in: IEEE Transactions on Components, Hybrids, and Manufacturing Technology 13 (1990), No. 2, New York, US, pages 331–340.

Furthermore a process for testing solder joints is known from Feldmann, K. and Sturm, J.: Closed Loop Quality Control in Printed Circuit Assembly, in IEEE Transactions on Components, Packaging and Manufacturing Technology—Part A 17 (1994) June, No. 2, New York, US, pages 270–278. The quality of the solder joints is tested by means of a X-ray inspection system. This system generates x-ray images of the solder joints as well as a list of actual defects as well as of pseudo defects and transmits said list to a repair station.

At the repair station a light beam is directed to solder joints having an actual defect or having a pseudo defect. Thereby a local indication of the solder joints having an actual defect or having a pseudo defect is generated on the circuit board. The operator at the repair station performs a defect verification on basis of said local indication of solder joints having an actual defect or having a pseudo defect.

On the basis of this prior art, the invention is based on the object of specifying a process and a circuit arrangement of the type mentioned at the beginning which improve the quality of the test of solder joints.

According to the invention, this object is achieved by a process and a circuit arrangement which are defined in the claims.

The invention is associated with a plurality of advantages. The operator at the repair work station receives comprehensive information on the position of a solder joint having a defect as well as an information on characteristics of this solder joint.

This comprehensive information is provided on a visual display device but not on the circuit boards having defective solder joints. Therefor, it is not required to transport the circuit boards having the actual defects or having pseudo defects to the repair work station; on the contrary said circuit boards can remain in another location. Thereby time and transport costs are saved.

The quality of the defect verification is considerably improved by means of the display of defective solder joints together with associated defect data. Thereby the number of repair operations based on pseudo defects is reduced on the one hand. On the other hand the information provided at the visual display device of the repair work station allows that operators having a relatively low qualification are able to perform the defect verification operations.

In summary, the invention allows that the tests of the quality of the solder joints can be performed in relatively short time and with high efficiency.

The invention will now be described with reference to the drawings, in which:

Figures 11, 12:
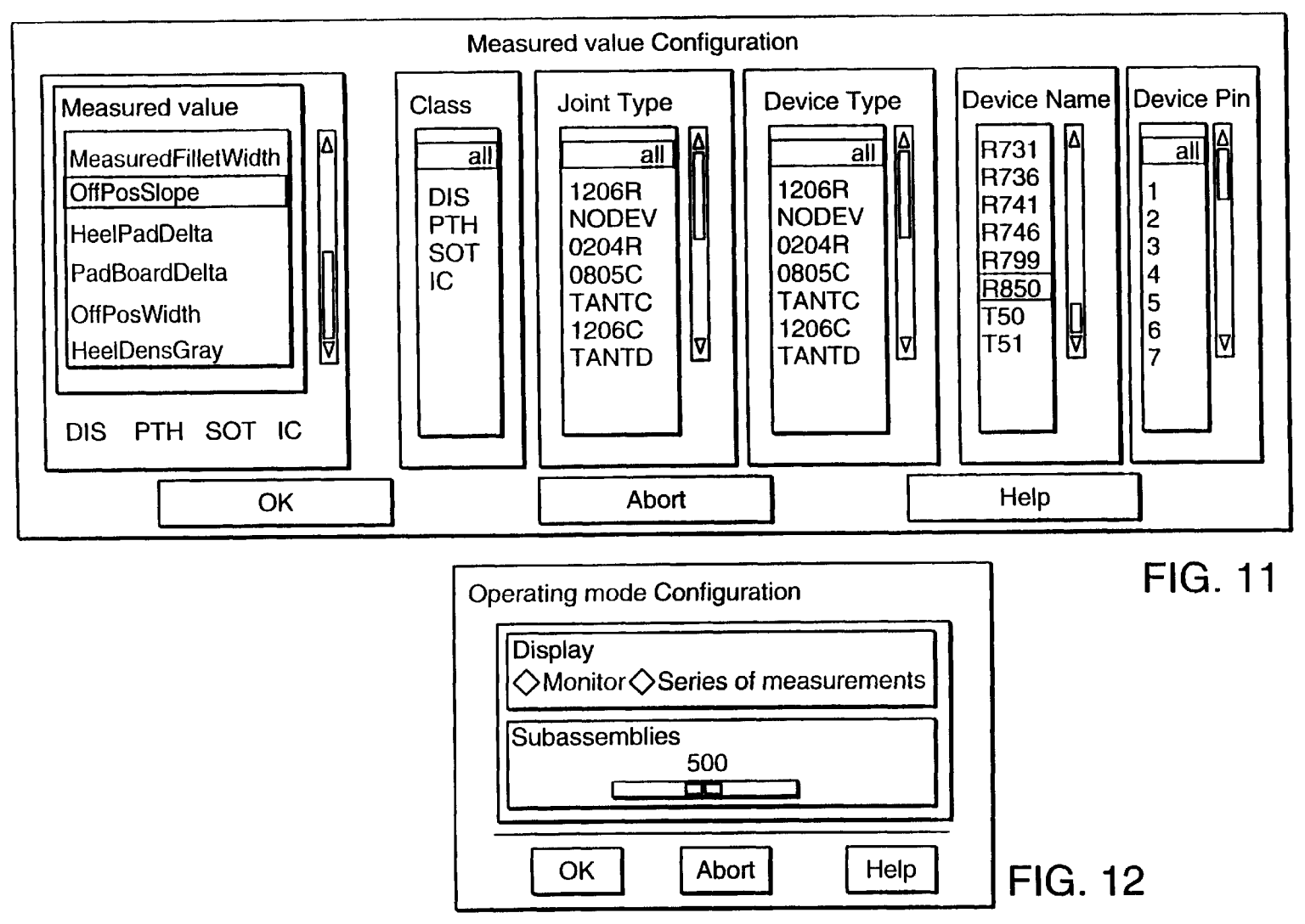

FIGS. 11 to 14 show monitor displays, formed within the context of the process according to the invention, in conjunction with the configuration of measured values and of reference values.

Figure 1:
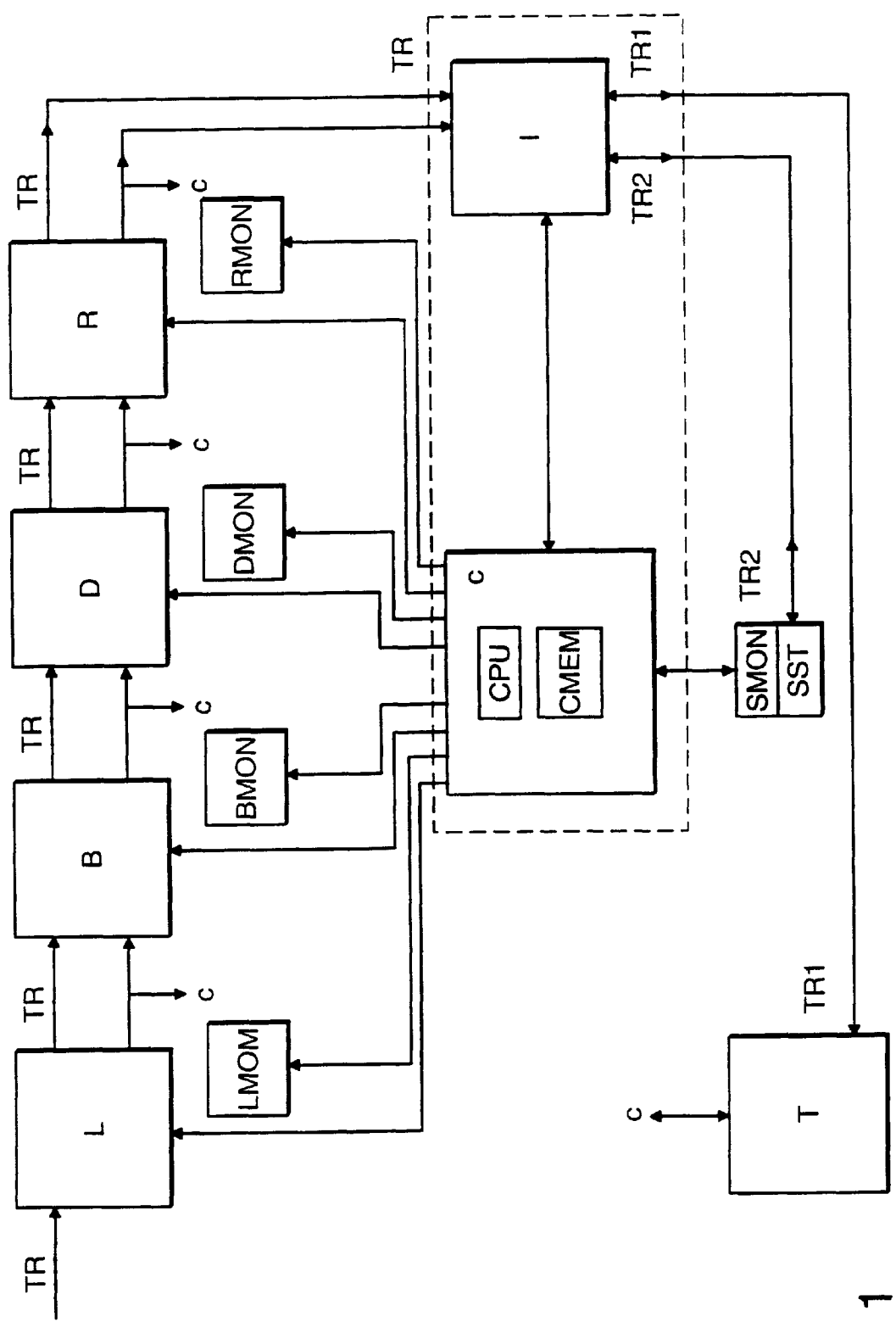
FIG. 1 shows an arrangement of devices in conjunction with carrying out the process according to the invention.

The arrangement illustrated in FIG. 1 comprises a first device L, which applies solder paste to printed circuit board blanks, a so-called dispensing device D, a second device B, which is formed by an automatic population device and populates the printed circuit boards, preferably using the SMD technique, with one or more components or subassemblies, a third device R, which is formed by a reflow soldering device, an X-ray inspection device I, a data processing device C, a repair workstation SST, which is also equipped for the verification of defect-free printed circuit boards (monitor SMON, which displays data generated by C) and has a keyboard (not illustrated) for controlling the monitor display or for carrying out dialogue with the data processing device C, and also comprises a device T which carries out electrical subassembly tests.

The devices L, D, B, R, I and T are devices which are known per se. The device L is, for example, a product from the MPM company bearing the product description Ultraprint; the device D is, for example, a product from the 3000 series from the Cama/lot company; the device B is, for example, an SMD automatic population device from the Siemens, Quad, Fuji or Panasonica MPM companies; the device R is, for example, a furnace from the BTU company or an appropriate product from the Elektrovert company; the device I is, for example, a product from the NICOLET (NIS) company bearing the product description CX13000/5000 and MV6000, and the device T is, for example, a product from the Hewlett Packard company bearing the product description HP 3070.

The devices L, B, D, R, and the repair workstation SST have assigned to them screen monitors LMON, BMON, DMON, RMON and SMON, which are connected to the data processing device C.

The data processing device C has assigned to it a control program defining the process according to the invention. It is indicated schematically in FIG. 1 with its controller CPU and with a memory CMEM which, inter alia, serves for the acceptance of the information which is formed within the context of the process according to the invention and to which access is made in order to form this information. The data processing device is connected to the devices L, D, B, R, I and T. The data processing device C receives from these devices first data which relate to the printed circuit boards treated in these devices, and/or second data which relate to the devices themselves. The first and/or second data can also be supplied by a device (e.g. L) of the device (e.g. B) that is in each case arranged downstream. The data processing device C supplies the devices L, B, D and R with control or regulation information which is formed as a function of solder-joint-specific quality information and/or the solder-joint-specific measured value information.

The monitors LMON, BMON, DMON, RMON and SMON are supplied by the data processing device C with, inter alia, solder-joint-specific quality information, solder-joint-specific measured value information and, if appropriate, statistical information about the frequency of occurrence of defects. This information is displayed on the monitors. Monitor displays of this type are illustrated in FIGS. 6 to 8 and 10.

The transport path of the printed circuit boards is designated in FIG. 1 by TR. From the output of the X-ray inspection device I, a first transport path TRI leads to the device T; transported on this transport path are printed circuit boards which have been detected as defect-free by the X-ray inspection device I or by the data processing device C. However, provision may also be made for printed circuit boards detected as defect-free to be supplied to the repair station SST for the purpose of verifying the freedom from defects.

In addition, a second transport path TR2 leads from the output of the X-ray inspection device I to the repair workstation SST; transported on this transport path are printed circuit boards which are detected as defective by the X-ray inspection device I or by the data processing device C. Following the repair, the printed circuit boards can be transported back on the transport path TR2 from the repair workstation SST to the X-ray inspection device I, where they are once more subjected to an inspection.

The X-ray inspection device I is capable, in a manner known per se, of forming solder-joint-specific information, either the information "solder joint defect-free" or the information "solder joint defective" being formed for each solder joint. In addition, the device I measures physical parameters of the solder joints, such as geometrical dimensions and/or the solder volume, and forms appropriate measured value information. A plurality of items of measured value information may be formed in relation to each solder joint.

To this end, the device I has the appropriate data-processing functionality; as an alternative to this, the corresponding data processing is carried out by the device C.

Overall, the arrangement illustrated in FIG. 1 constitutes a control arrangement with which printed circuit boards may be pre-treated with regard to their population with electronic components, may be populated, soldered and checked for their quality.

The solder-joint-specific quality information and/or solder-joint-specific measured value information which characterizes measured physical parameters of checked solder joints is used for the repair of checked, defective solder joints, for the verification of checked solder joints and/or for the control of the production of further solder joints on-line, that is to say in the continuous production process in which the solder joints are tested.

For instance, the solder volume of the solder joints and/or the height at least of one meniscus of the solder joints and/or dimensions of the contact area of the solder joints on the printed circuit board are measured, and the measured value information is formed from these measured values.

In this connection, provision is further made that, using the solder-joint-specific quality information and/or using the solder-joint-specific measured value information, a test is carried out for defective solder joints as to what type of defect is present. This testing may be performed by means of algorithms which are known per se and which are described, for example, in EP 0 236 001 B1. These defect types include, for example, "cold solder joint" and "incorrect positioning of a solder joint".

The device I forms so-called tag files, that is to say files in which the defect messages for one printed circuit board are contained.

The control program that is assigned to the controller CPU of the data processing device C allocates the defects detected to a defect type or a defect class in each case. For instance, the defect classes "solder paste defect", "population defect" and "soldering defect" are provided.

For example, the defects "deficient solder" and "excessive solder" are defects of the defect class "solder paste defect"; the defect "offset of a populated component" is a defect from the defect class "population defect"; and "wetting defect" (solder not correctly fused with the pin) is a defect from the defect class "soldering defect".

A defective solder joint may have a plurality of defects, so that such a solder joint may be assigned to a plurality of defect types or defect classes.

Depending on the respective defect class (solder paste defect, population defect, soldering defect), the data processing device supplies the device L, B or R with control information. If the data processing device has detected, for example, a defect from the defect class "solder paste defect", it adjusts the device L. If the data processing device has detected, for example, a defect from the defect class "solder paste defect" and, in addition, a defect from the defect class "population defect", it adjusts the device L and the device B. The control information may comprise, for example, a defect warning signal, which can be displayed on the devices L, B or R or on the associated monitors, or may comprise data which modify the operation of the respective device. Examples of this are changes to the quantity of solder paste supplied in each case and changes to the temperature of the soldering means.

A defect may have several causes. For instance, the defect "deficient solder" may arise from a "solder paste defect" (=defect during the application of solder paste) and from a "population defect" (=defect during population, for example component is offset in such a way that only part of the area (lead) that is normally to be wetted of the component is supplied with sufficient solder), so that in this case the defect "deficient solder" has the two defect classes "solder paste defect" and "population defect" assigned to it.

For predefinable points on the printed circuit board to be tested, the device I forms at least one measured value, it also being possible for provision to be made for a plurality of measured values to be formed for a specific point on the printed circuit board. For each predefinable solder joint, the device I provides an item of measured value information or a combination ("rule") of several items of measured value information to the data processing device C.

The control program that is assigned to the controller CPU of the data processing device C is configured in such a way that each item of measured value information is compared with a desired value (defect limit value) or with a lower and upper limit of a permissible range. The desired values (defect limit values) or the limits of permissible regions are predefinable or have a fixed relationship with a statistical mean which has been given by a process recognized to be good. Provision may be made for the limit values to be able to deviate only by predefinable ranges in a measured-value specific manner from the respective statistical mean of a process recognized to be good.

If a combination of items of measured value information consists of three items of measured value information, for example, then each of the three items of measured value information is compared with its associated desired value (defect limit value), which must neither be overshot nor undershot, or with the lower and upper limit value of a permissible range.

If the result is that each item of measured value information of the combination of items of measured value information does not overshoot the associated desired value which must not be overshot, or does not undershoot the associated desired value which must not be undershot, or lies within the limits of the permissible range, then the ("first") solder-joint-specific item of quality information "solder joint defect free" is formed. Otherwise, the ("second") solder-joint-specific item of quality information "solder joint defective" is formed.

If the second item of quality information "solder joint defective" is to be formed, that is to say the measured value overshoots a permissible upper limit value or if it undershoots a permissible lower limit value, then, in relation to the relevant solder joint, that item of measured value information that has the greatest relative deviation from the respectively associated limit value is ascertained.

If the result is that, for example, the second item of measured value information of the combination of items of measured value information has the relatively greatest deviation from its associated desired value, one and only one of the devices L, B, D or R is adjusted, depending on this item of measured value information.

Provision may be made for those two items of measured value information of a combination of items of measured value information which have the relatively greatest deviations from their respective defect limit value in each case to be ascertained. If, in the example of the combination of items of measured value information comprising three items of measured value information, this applies to the first and the second items of measured value information, then depending on these two items of measured value information (first and second items of measured value information), then it is only the device L, B, D or R which is responsible for the occurrence of the relevant defect which is adjusted. It is also possible for a plurality of devices L, B, D, R to be the cause of defects for the occurrence of combinations of items of measured value information. In this case, the appropriate devices are adjusted.

Furthermore, it is also possible for three and more items of measured value information of a combination of items of measured value information to be evaluated in this way, in order in each case to adjust those devices L, B, D or R which are responsible for the respective defect.

The defect limit or desired values are predefinable and preferably correspond to the statistical means of a process recognized to be good; however, the defect limit or desired values may also deviate from these means.

If, for example, the width of a predefinable solder joint is x millimeters as a statistical mean (at the peak of the Gaussian distribution), then it is possible for x+a, x−b, 1.1x, etc. to be provided as defect limit values. It is thus possible for typical defect characteristics to be filtered out. x may be 20 millimeters and the predefinable lower defect limit value may be 16 millimeters (x=4 millimeters). A current measured value at 18 millimeters is then judged as adequate. The relative deviation of the current measured value from the defect limit value is then (18−16)/18×100%=11.11%.

As an example, a combination of items of measured value information consists of the following three items of measured value information:

| | |
|---|---|
| Measured value information item 1: | measured_width (measured solder joint width) = 22 millimeters |
| Measured value information item 2: | heel solder (amount of solder) corresponding to 6000 standardized grey-value components in a defined testing window |
| Measured value information item 3: | heel pad delta (solder meniscus height) = 1500 micrometers. |

The statistical means are, for example, in the case of measured value information item 1: 20 millimeters in the case of measured value information item 2: 10,000 standardized grey-value components in the case of measured value information item 3: 3000 micrometers.

Hence, the greatest relative deviation results for the measured value information item 3. This measured value information item 3 is assigned a first item of information which identifies the defects "soldering defect" and "solder paste defect". Using the first item of information, the devices L and R are adjusted.

If, in the case of this example, the two items of measured value information having the greatest relative deviations are ascertained, then these are the measured value information item 3 and the measured value information item 2. This combination of the measured value information items 3 and 2 is assigned a second item of information which identifies the defect "soldering defect". Using this second item of information, the device R is adjusted.

If all three items of measured value information from the combination are evaluated, this combination is assigned a third item of information which likewise identifies the defect "soldering defect". Using the third item of information, the device R is likewise adjusted.

The first, second and third items of information firstly indicate which of the devices L, B, D or R is adjusted. In addition, the first, second and third items of information in each case indicate a controlled variable, that is to say operational parameter or operational parameter changes of the respective device (for example, an increase or reduction in the quantity of solder paste to be applied, an increase or reduction in the solder to be applied).

The three defect classes "population defect", "solder paste defect" and "soldering defect" have a plurality (for example the following) defect types assigned to them:

| | |
|---|---|
| "Wet.Gullw. | A", (wetting of gullwing) |
| "Wet.J-leg | B", (wetting of J-leg) |
| "Wet.quad.SMD | C", (wetting of cuboidal SMD) |
| "SMD_offset | D", |
| "other_sol_def. | E", |
| "not_soldered | F", |
| "solder_bridge | G", |
| "bent_away/up | H", (connecting pin bent away/bent up) |
| "SMD_offset | I", |
| "other_sol_def. | J", |
| "solder_beads | K", |
| "INSUFF_TOE | L", (thin solder joint) |
| "SMD_bubble | V", (solder bubble) |

In addition, provision may be made for the detected defects or items of measured value information to be assigned to a defect type—such as listed above, for example—and for the defect types to be assigned to a defect class (solder paste defect, population defect, soldering defect).

The solder-joint-specific quality information and/or the solder-joint-specific measured value information which characterizes the measured physical parameters of checked solder joints, and/or statistical information about the frequency of occurrence of defects are displayed on the monitors LMON, BMON, RMON which are assigned to the devices L, B and R.

The data processing device C and the repair workstation SST may, for example, be designed in the following two variants:

| 1. PC variants | |
|---|---|
| CPU | HP Vectra VL2 4/66 |
| | HP Vectra VL2 5/60 |
| Main memory | 24 MB |
| Hard disk | 500 MB |
| Swap | 60 MB |
| Graphics card | Ultra VGA 1024 × 768 pixels |
| Monitor | 15" or 17" |
| Operating system | Solaris x86 2.4 |
| Network card | 16-bit BNC, TP, AOI |

| -continued | |
|---|---|
| Options | |
| Input | Numeric keypad |
| | Trackball |
| | RS-232 bar-code scanner |
| Light pointer | Heeb OM-500 |
| | Royonic 500 |
| Printer | HP DeskJet 1200C/PS |
| | HP LaserJet 5MP |
| Data backup | Magnetic tape (QIC or DAT) |
| | Magneto-optical disk drives |

| 2. Workstation variants | |
|---|---|
| CPU | Sun SparcStation 4 |
| | Sun SparcStation 5 |
| Main memory | 32 MB |
| Hard disk | 1 GB |
| Swap | 60 MB |
| Graphics card | 1024 × 768, 1152 × 900 pixels |
| Monitor | 15" or 17" |
| Operating system | Solaris 2.4 |
| Network card | incorporated |
| Options | |
| Input | 3½" floppy disk drive |
| | Numeric keypad |
| | RS-232 bar-code scanner |
| Light pointer | Heeb OM-500 |
| | Royonic 500 |
| Printer | HP DeskJet 1200C/PS |
| | HP LaserJet 5MP |
| Data backup | Magnetic tape (QIC or DAT) |
| | Magneto-optical disk drives |

The control program defining the process according to the invention is, for example, a UNIX application which is mounted on the Solaris operating system from SunSoft.

The control program realizes, inter alia:

a) a display of the X-ray inspection results generated by the device I;

b) a display of the defects found during the X-ray inspection, step by step in a graphic representation of the printed circuit board layout;

c) a display of the defects found during the X-ray inspection, step by step with the aid of a laser/light pointer on the original printed circuit board;

d) a display of defects (accumulation of defects at one or more points on the printed circuit board) in a graphic representation of the printed circuit board layout;

e) verification, acknowledgement and further processing of the defects found during the X-ray inspection, if necessary step by step by an operator of the repair workstation SST, using a dialogue menu; and f) storage of processed defect data as an interface to a program module or to quality management systems.

The abovementioned elements of the control program are described below:

a) display of the X-ray inspection results generated by the device I in text form.

This display is produced on the SMON monitor of the repair workstation SST.

The program working area comprises a main window with a menu bar. Further windows may be superimposed.

The menu bar comprises the following menus with the options:

| | |
|---|---|
| File | File functions |
| Editor | Call up a text editor |
| Exit | Exit from program |
| Operating mode | Select operating modes |
| Individual defect | Individual defect display |
| Defect overview | Display of the defect overview |
| X-ray image | Display of the X-ray image |
| Configuration | Configuration settings |
| Light/laser pointer> | Select the light/laser pointer |
| Royonic 500 | Royonic 500 light pointer |
| Heeb laser | Heeb LL-2A or OM-500 |
| Operating mode> | Setting the standard operating mode(s) |
| Individual defect | Individual defect display |
| Defect overview | Defect overview |
| X-ray image | X-ray image window |
| File paths> | File path specification |
| CXI tag files | Path to the CXI tag files |
| X-ray image files | Path to the X-ray views |
| CAD files | Path to the CAD files |
| Results files | Path to the results files |
| Defect type reference | Path to the defect type reference file |
| Verification dialogue> | |
| GOOD boards auto. | Automatically accept defect-free boards |
| Options> | Option menu for various settings |
| Symbol bar | Superimpose and hide symbol bar |
| Save on exit | Save settings on exit |

The above-described menu bar is adapted appropriately in the event of changed or additional operating steps.

b) Display of the defects found during the X-ray inspection, step by step in a graphic representation of the printed circuit board layout b1) Operating mode: individual defect display The control of the individual defect display by the operator of the repair workstation SST is carried out using a dialogue window, which contains the elements Header, Option group Display, Option group Page, Defect list, Buttons, Next, Back, True defect, Pseudo defect, New defect, Change defect type, Next component, Done, Abort In the "Header", the data from the top of the data from the X-ray system I are displayed.

Using the "Option group Display", the operator is able to select the display forms for the individual defect display. The options available are "Layout", for the representation of the graphical printed circuit board layout on the monitor, and "Pointer", for the display on the original printed circuit board with a light/laser pointer.

With the aid of the "Option group Page", the side of the printed circuit board that is displayed is selected. Those available are upper side and lower side.

The "defect list" contains all the defects on the printed circuit board that were found by the X-ray system or added by the operator. The defect which is currently displayed in the printed circuit board layout and/or indicated by the light/laser pointer is highlighted in the defect list.

The button "Next" displays the next defect in the defect list in the printed circuit board layout and/or using the light/laser pointer.

The button "Back" displays the preceding defect in the defect list in the printed circuit board layout and/or using the light/laser pointer.

The button "True defect" marks the current defect as a true defect.

The button "Pseudo defect" marks the current defect as a pseudo defect.

The button "New defect" inserts a new defect into the list and shows the defect in the printed circuit board layout and/or using the light/laser pointer.

The button "Change defect type" permits the defect type of a defect that has already been marked to be changed again.

The button "Next component" jumps to the next component in the defect list. If this button is pressed, the individual defects are erased, and the defect code for the total component defects is entered in the results file.

The button "Done" or the button "Enter" after the last defect entry enters the marked true defects and the marked pseudo defects in the results file and terminates the verification operation for this subassembly. In the event of a premature abort, an abort message is entered in the results file as the last line (see also the "Abort" button).

The button "Abort" closes the dialogue window and the window with the graphical printed circuit board layout and/or moves the light/laser pointer into a rest position. An abort message is entered in the results file (see below) as the last line.

Via a standardized software interface, the selected defect is transferred to the program module for the display in the graphical printed circuit board layout and using the light/laser pointer.

Figures 2, 3:
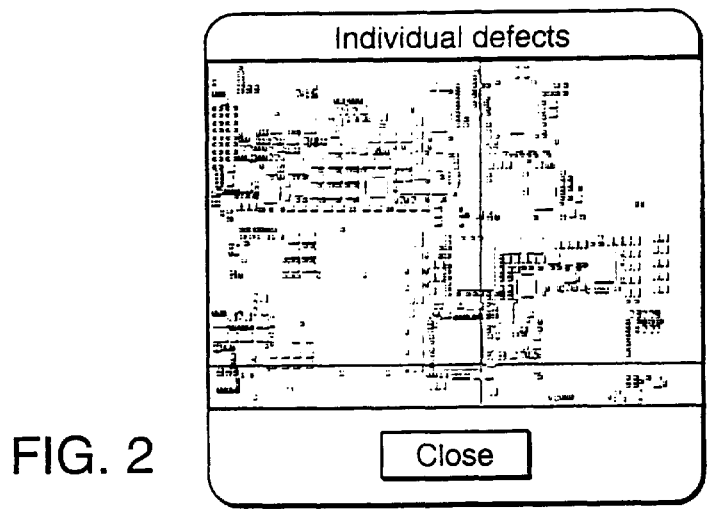
FIG. 2 shows a monitor display, formed within the context of the process according to the invention, of an individual defect.
FIG. 3 shows a monitor display, formed within the context of the process according to the invention, of a defect list.

If the display of the printed circuit board layout is activated, then each defect in the defect list is displayed by means of a marking in a graphical printed circuit board layout, which is produced from CAD data that describe the printed circuit board. A display is illustrated in FIG. 2, it being the case that, for example, the solder joint marked by the (external) arrow in the actual screen display is assigned a marking which cannot be seen in FIG. 2.

In a standard setting, all the subassemblies of the printed circuit board are displayed in the graphical layout. Defect data are accepted via a standardized software interface, and the appropriate defects are displayed. Defects are highlighted in colour.

It is possible to display the entire printed circuit board or only a detail, preferably on an enlarged scale.

b2) Operating mode: defect overview

This operating mode makes it possible to display the marked true defects from the defect list, together or separated by defects, on a graphical representation of the printed circuit board layout.

The defects which the device I detects are assigned to the defect types "population defect", "soldering defect" and "solder paste defect". "Population defects" are displayed in blue, "soldering defects" in yellow and "solder paste defects" in green. The side (upper side/lower side) of the printed circuit board on which the components are located is indicated in the window.

Illustrated in FIG. 3 is an example of a defect list displayed on the screen.

b3) Operating mode: X-ray image display

Figure 4:
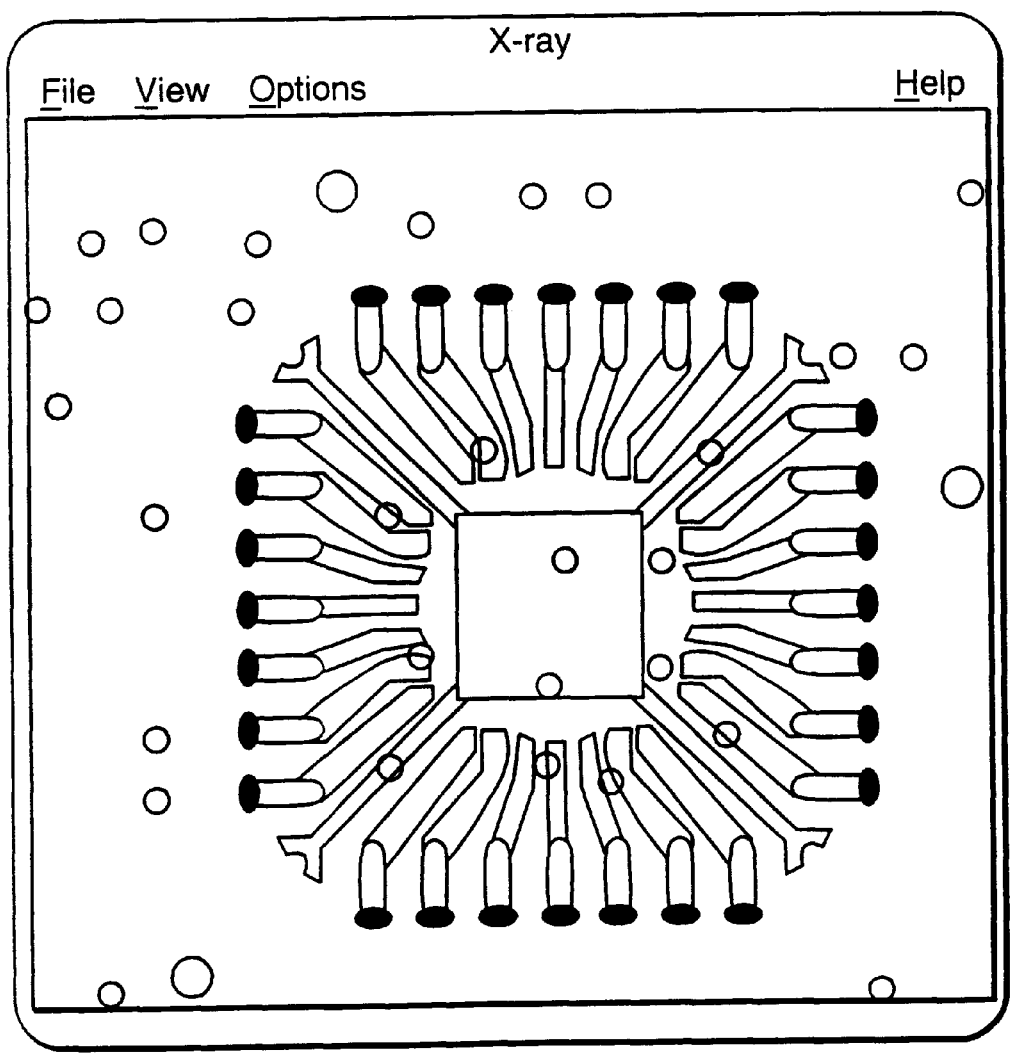
FIG. 4 shows a monitor display, formed within the context of the process according to the invention, of an X-ray image of a printed circuit board having solder joints.

In a separate window, it is possible for the X-ray image matching the data generated by the device I to be displayed. An example of such a window is illustrated in FIG. 4, a defective solder joint on the right in the window being marked by a square frame. It is optionally possible for the complete components list of the image to be superimposed on this window.

c) Display of the defects found during the X-ray inspection, step by step with the aid of a laser/light pointer on the original printed circuit board;

If the display using the light/laser pointer is activated in the dialogue window, then the defect is indicated on the original printed circuit board using a point of light. For example, it is possible to use the Royonic light pointer 500 or Heeb Laserlite LL-2-A or 500 light/laser pointers.

d) Display of defects (accumulation of defects at one or more points on the printed circuit board) in a graphical representation of the printed circuit board layout.

Figure 5:
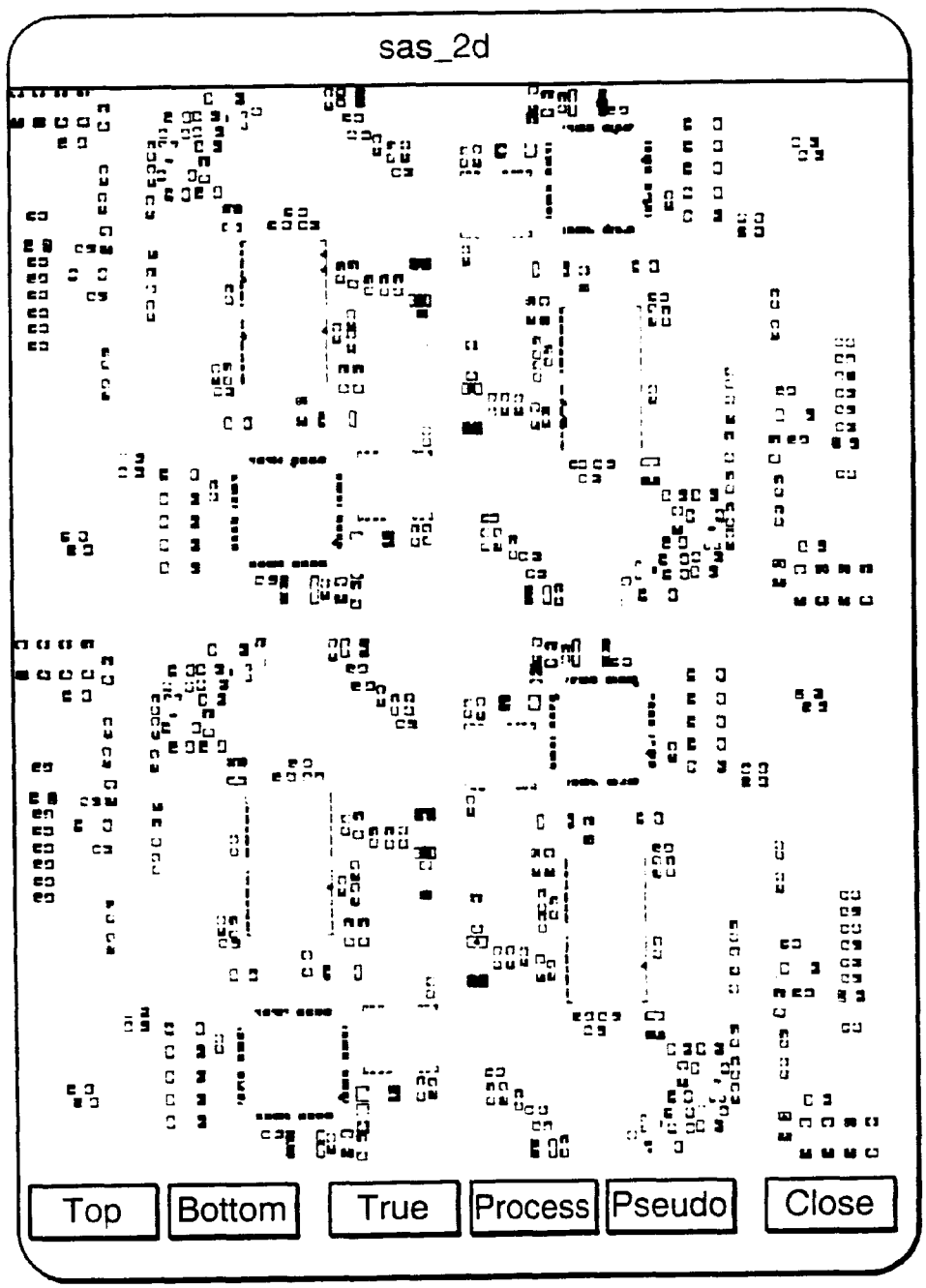
FIG. 5 shows a monitor display, formed within the context of the process according to the invention, of defects (accumulation of defects at one or more points on the printed circuit board) in a graphic representation of the printed circuit board layout.
Figure 6:
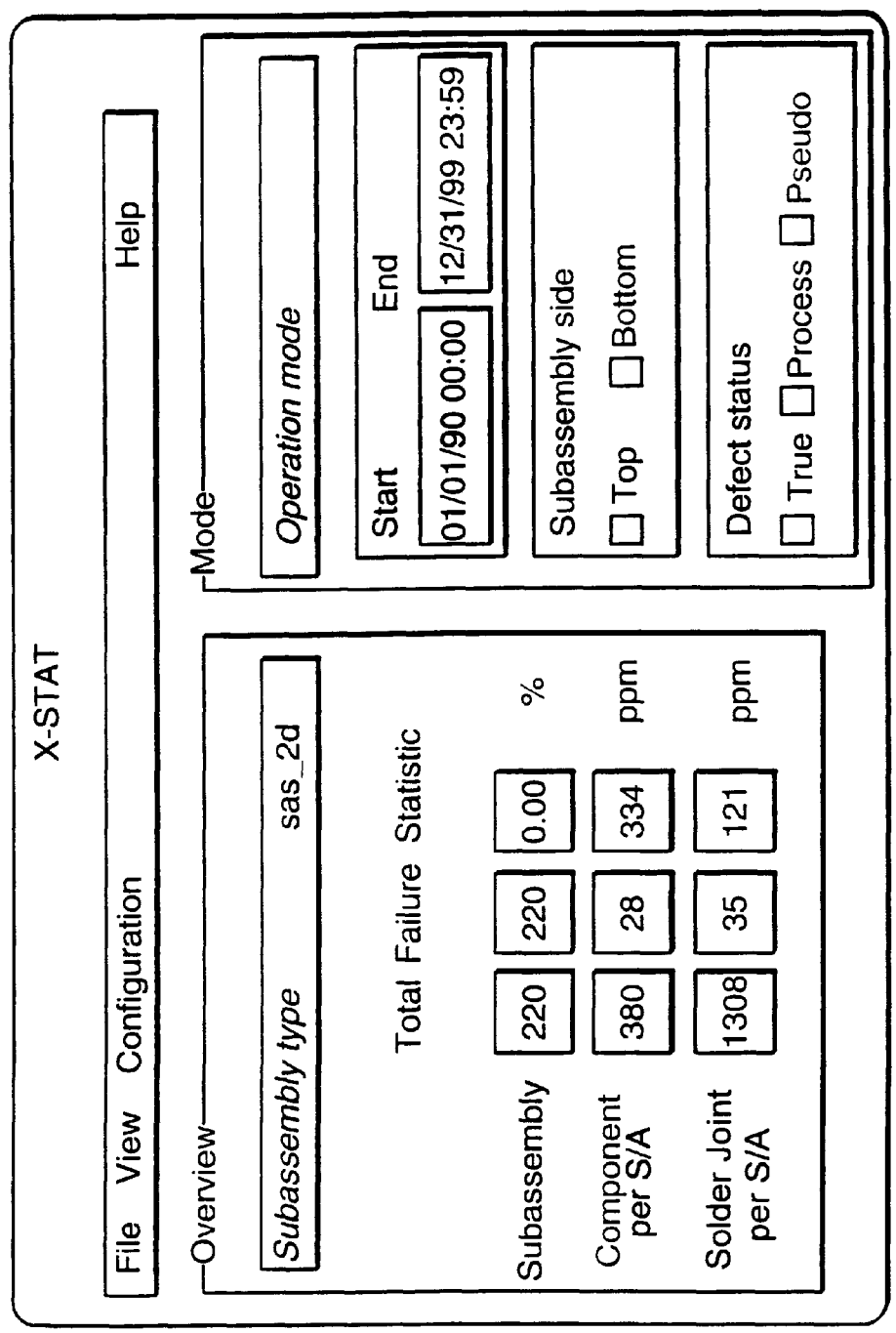
FIGS. 6, 7 and 8 show monitor displays, formed within the context of the process according to the invention, of defects in a statistical evaluation.
Figure 7:
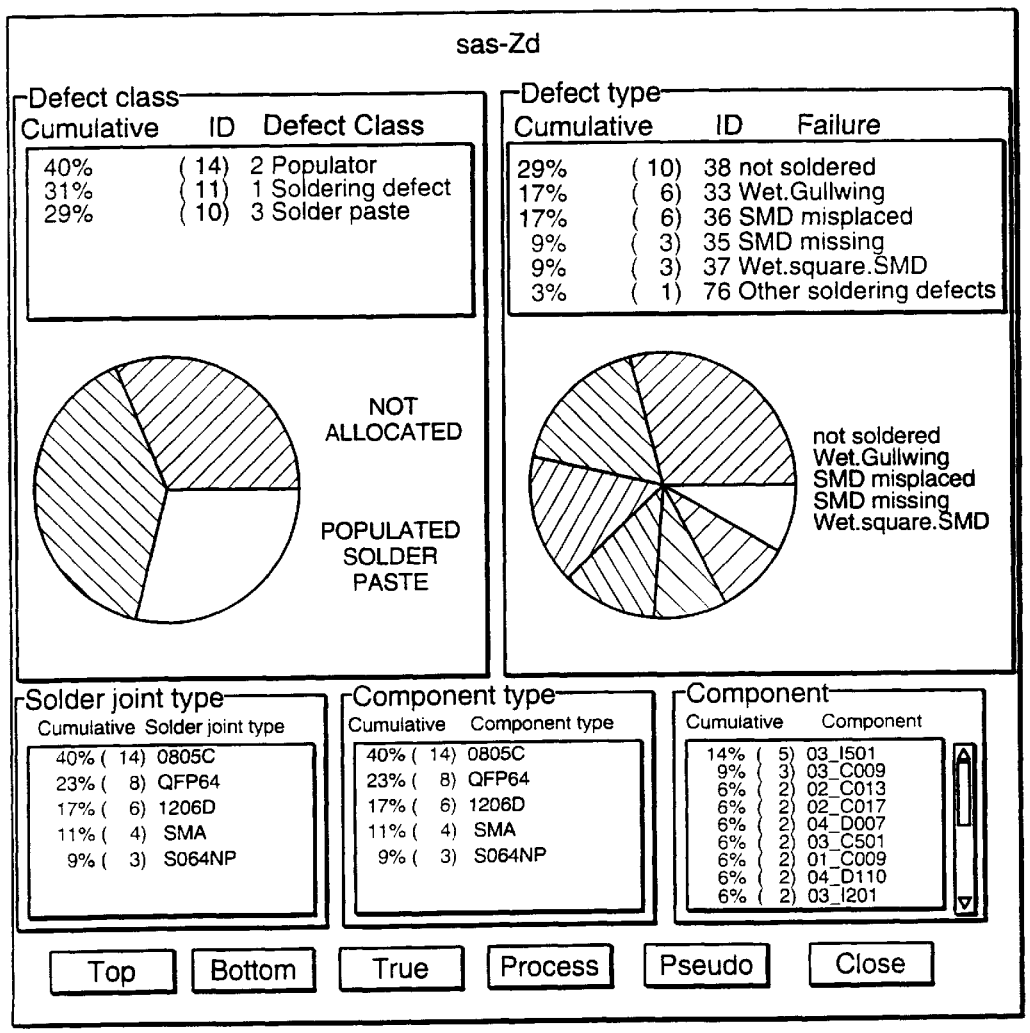
Figure 8:
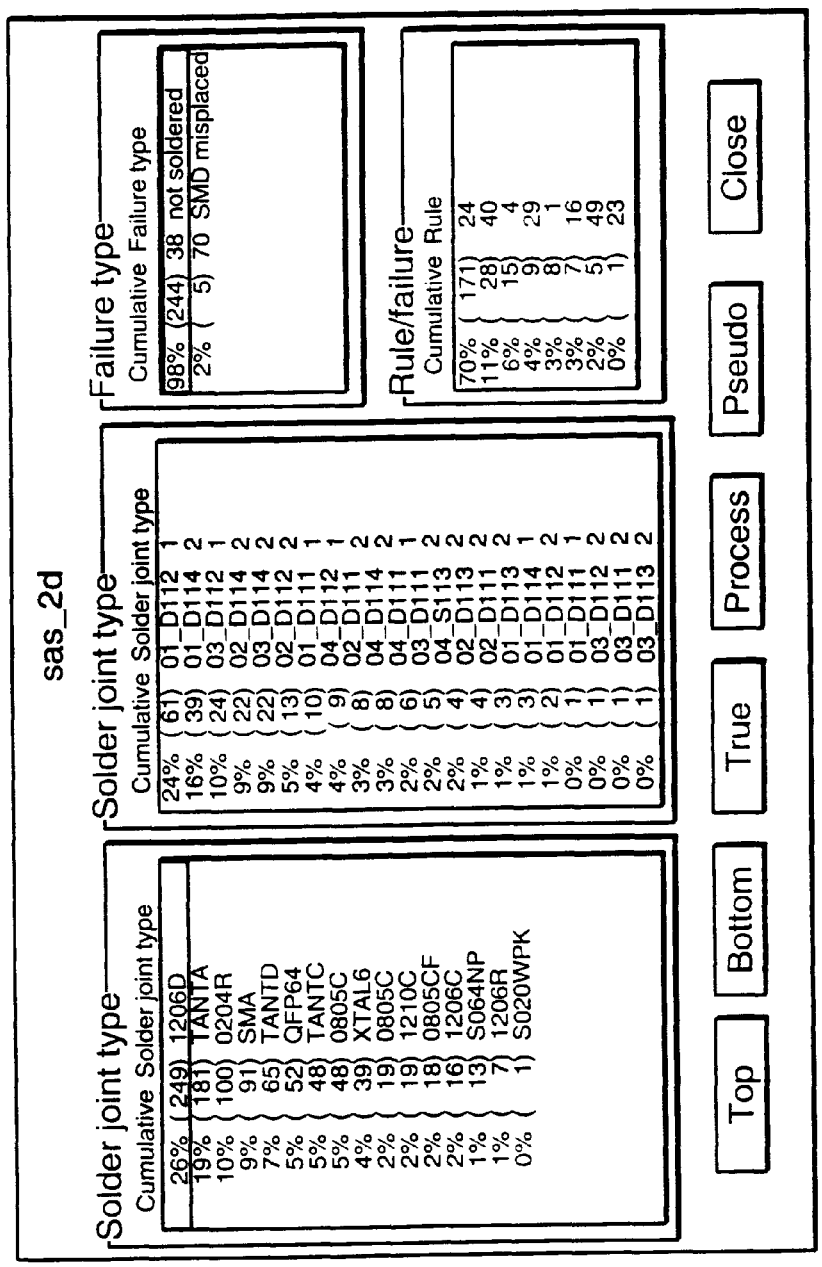

An example of a display of this type is illustrated in FIG. 5, it not being possible in FIG. 5 to recognize the actual defect data which, in the actual screen display, are assigned adjacent to the associated solder joints. Further displays of defects in a statistical evaluation are illustrated in FIGS. 6, 7 and 8.

e) Verification, acknowledgement and further processing of the defects found during the X-ray inspection, optionally step by step by an operator of the repair workstation SST using a dialogue menu.

Figure 9:
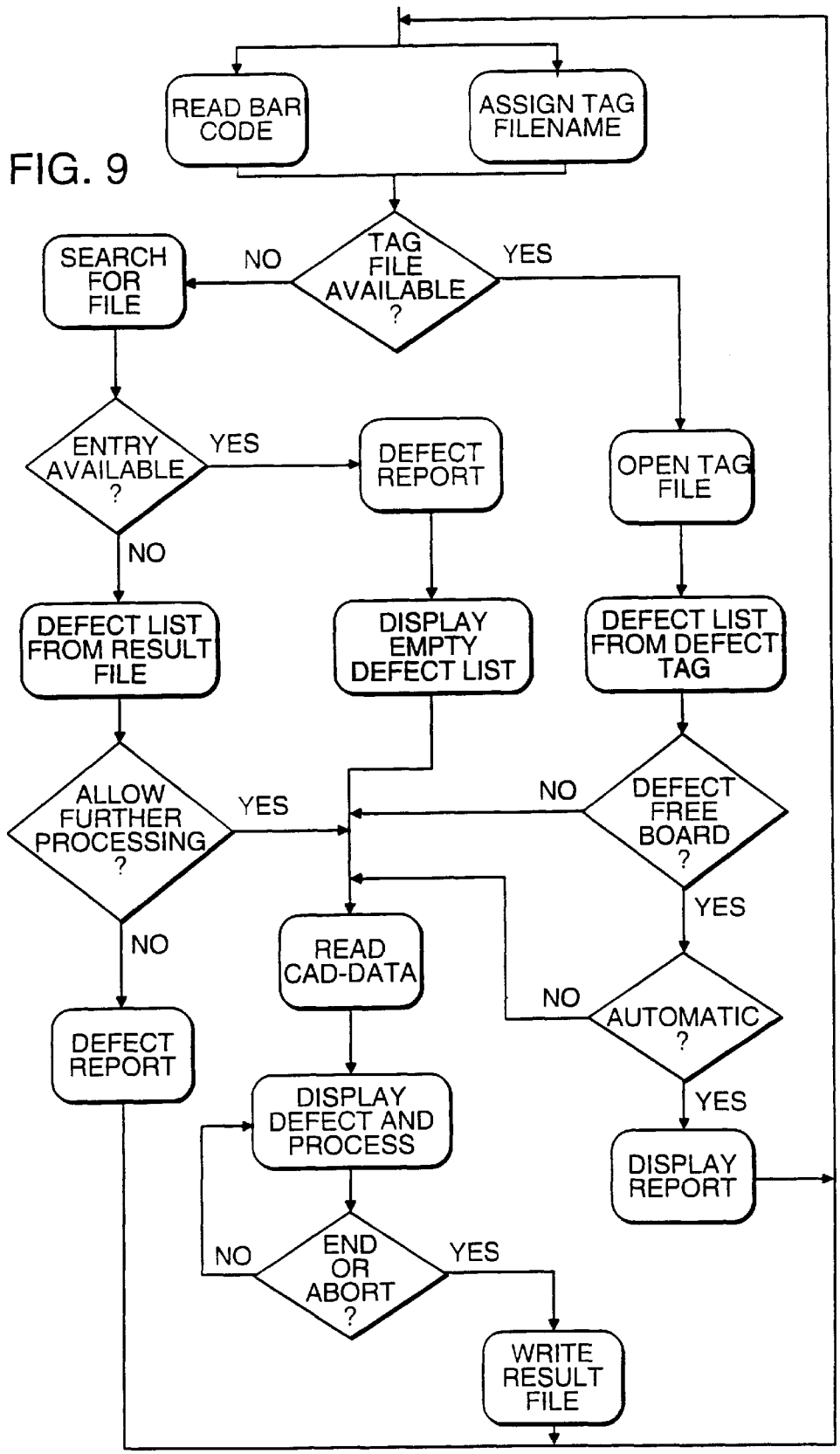
FIG. 9 shows the sequence of a cycle in conjunction with the verification of defect-free printed circuit boards and to the repair of defective printed circuit boards.
Figure 10A:
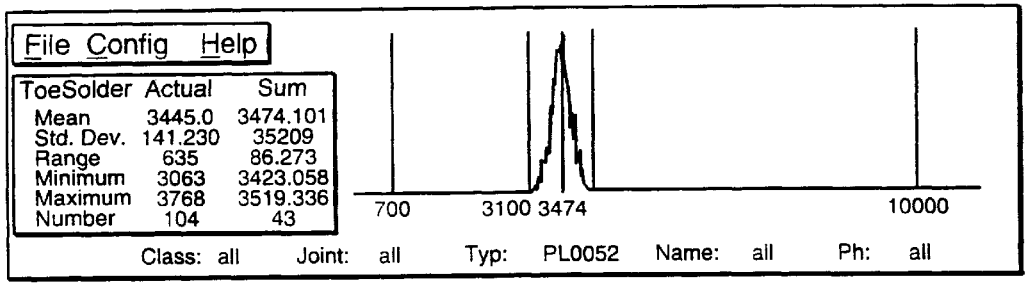
FIG. 10 shows monitor displays, formed within the context of the process according to the invention, of measured values and windows for measured value selection.
Figure 10B:
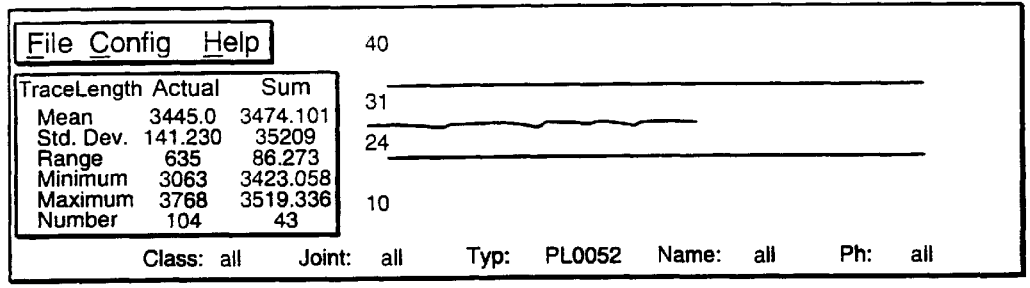
Figure 10C:
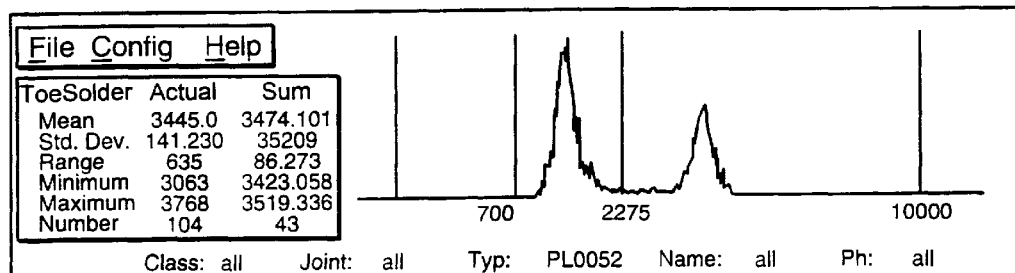
Figure 10D:
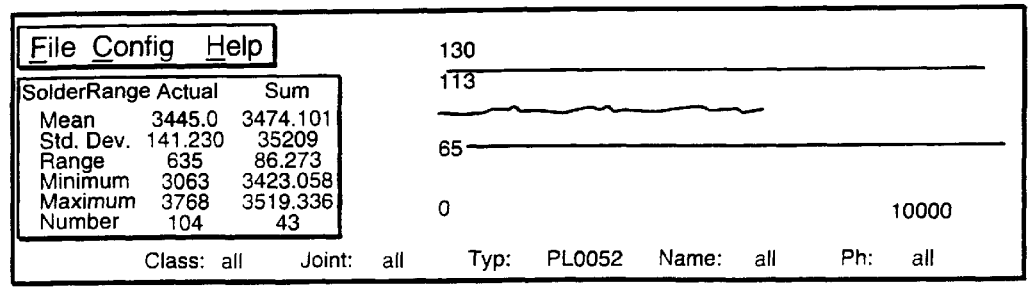
Figure 10E:
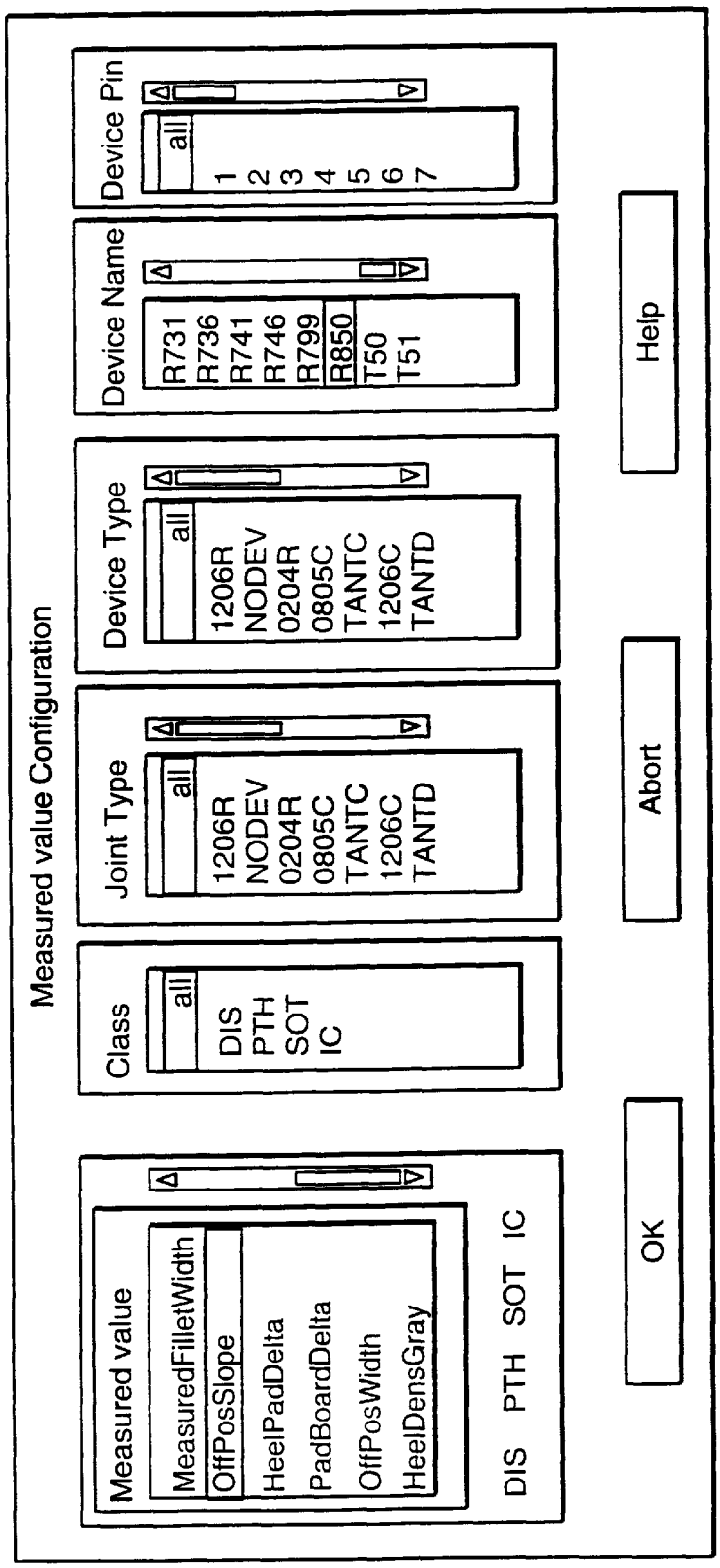

The sequence of a cycle in conjunction with the verification of defect-free printed circuit boards, and the repair of defective printed circuit boards, is described below, and is also illustrated in FIG. 9.

For the verification and repair of printed circuit boards, it is necessary for the individual defect display operating mode to be activated. A repair cycle begins with reading the printed circuit board number using a bar-code reading pen.

Alternatively, the repair may also begin with the selection of a defect tag file via keyboard or mouse.

On the basis of the printed circuit board number read, the associated tag file for the printed circuit board is sought and opened, and the header and the defect list are read. If a defect-free printed circuit board is involved, then a distinction is made between two cases, depending on the GOOD_ BOARDS switch:

GOOD_BOARDS=AUTO

A message is displayed to say that the printed circuit board is defect free, and an entry in the results file is automatically generated, or a new results file is created, in which the defect-free printed circuit board is noted.

GOOD_BOARDS=MANU

The procedure continues as in the case of defective printed circuit boards, with the exception that the defect list is empty.

In the case of a defective printed circuit board, on the basis of the subassembly identification number contained in the header of the tag file, the CAD files are sought and opened and the geometric data of the subassembly are read. If the subassembly identification number of the current printed circuit board is identical with that previously tested, then the renewed reading of the geometric data is omitted.

The defect list is displayed in the dialogue window, the first defect is marked and indicated on the printed circuit board layout on the screen and/or using the light/laser pointer.

With the aid of the switching areas in the dialogue window that were described in the section "individual defect display", the defects in the list can then be classified and marked by the operator. After a defect has been marked, a jump is automatically made to the next defect. If the operator has marked (processed) all the defects in the list, or marked them as a total defect using "next component", then these defects are entered in the results file.

Following the processing of the board, the test files relating to the printed circuit board (I-tag files, X-ray images) are removed, if a switch DEL_TAG=On is set. The standard value is DEL_TAG=Off.

If there is no test tag available for the current board, the results file is looked through following an entry for this board or the corresponding directory is looked through for a results file for this board, and the following is done:

Output of a defect message if the board is also not present in the results file or if no dedicated results file exists for this board.

If a defect-free board is concerned, from which the tag file is available, then the procedure is as described above, depending on the GOOD_BOARDS switch.

If the renewed processing of the board is concerned (no tag file, but entry in the results file or a dedicated results file), then the further operation is affected by the REWORK_BOARDS switch. If the entry in the configuration file is REWORK_BOARDS=On, then the printed circuit board can be processed once more using the defect data from the results file. If, on the other hand, the entry is REWORK_BOARDS=Off, then a message is output that repeated processing is not possible.

f) Storage of processed defect data as interface to a program module or to quality management systems.

The data processing device C processes, inter alia, population data, using the following fields:

| Field name | Data format | Description |
|---|---|---|
| Joint | long int | Consecutive number of the solder joint (I to max_joint) |
| Pin/Device | long int | Consecutive number of the pin per component (1 to max_pin) |
| Pin X | long int | X-coordinate of the pin related to the board origin |
| Pin Y | long int | Y-coordinate of the pin related to the board origin |
| Pad X | long int | Pad length in X-direction |
| Pad Y | long int | Pad length in Y-direction |
| Side | char | Subassembly side (T | B) |
| Device name | char[15] | Designation of the component (without '\0') |
| Device type | char[25] | Designation of the component type (without '\0') |
| View | long int | Consecutive number of the view (1 to no_of_views) |
| View X | long int | X-coordinate of the pin in relation to the view |
| View Y | long int | Y-coordtnate of the pin in relation to the view |

In addition, the data processing device C processes a defect type reference file.

As already described, each defect detected by the device I is assigned a defect class "population defect", "soldering defect" and "solder paste defect". The contents of the file are organized into individual data sets having, for example, four data fields. Each line of the file describes one reference. The fields have the following meanings:

| Field name | Field length | Description |
|---|---|---|
| Defect | 3 characters (long) | Defect number |
| Defect message | 20 characters | As per defect tag |
| Defect class | 3 characters (long) | Defect class |
| Defect class message | 20 characters | Message for screen outputs |
| Colour | 10 characters | Colour with which this defect is displayed on the screen |

-continued

| Field name | Field length | Description |
| --- | --- | --- |
| Symbol | 10 characters | Symbol that is used to display the defect on the light/laser pointer |

An example of a defect type reference file is configured as follows:

| Defect type | Defect class | Colour | Symbol |
| --- | --- | --- | --- |
| 65;2503 solder link | a;1;soldering defect; | yellow; | point |
| 40;2503_Wet.Gullw. | H;1;soldering defect; | yellow; | point |
| 18;3208 offset row | 2;4;population defect | blue; | arrow |

For each printed circuit board, a dedicated results file may be generated. As an alternative to this, a common results file can be generated for a plurality of processed printed circuit boards, in particular for all processed printed circuit boards. For the two types of results file, each defect generates an entry in this file.

For the subassembly handled, a header dataset is created first, this consisting of the following fields:

| Field name | Field length | Description |
| --- | --- | --- |
| Dataset type | 1 character | always "H" in header line |
| Serial number of the subassembly | 25 characters | as per defect tag or bar-code |
| Blank ID | 2 characters (long) | as per defect tag |
| Subassembly type | 20 characters | as per defect tag |
| Test system ID | 12 characters | as per defect tag |
| Date of inspection | dd:mm:yy | as per defect tag |
| Time of inspection | hh:mm:ss | as per defect tag |
| UserID of tester | 4 characters (long) | as per/etc./passwd file |
| Date of repair | dd:mm:yy | as per system time |
| Time of repair | hh:mm:ss | as per system time |
| Status | 1 character (long) | 0 = no repair; 1, 2 . . . number of repairs |

Adjacent to this header line there follows, for each defect, a data line which consists of the following fields.

| Field name | Field length | Description |
| --- | --- | --- |
| Dataset type | 1 character | always "D" in data line |
| Component name | 15 characters | as per defect tag |
| Pin number | 3 characters (long) | as per defect tag |
| Defect code 1 | 3 characters (long) | as per defect code table |
| Defect code 2 | 3 characters (long) | as per entry by the tester |
| Rule | 2 characters (long) | as per defect tag (DL field) |
| Defect class | 3 characters (long) | as per reference table |
| Defect status | 2 characters (long) | Code (0 = confirmed, 1 = changed, 2 = pseudo) |

The above-described process may be one control program from a plurality of program modules assigned to the controller CPU. The control program, which is preferably of modular construction, may have further program modules. Each program module can be used on its own or together with one or more other program modules.

A program module of the control program is, as already described, configured in such a way that the X-ray images generated by the device I, or electronic images generated from these and images generated from CAD data and relating to the graphical layout of the printed circuit boards may be displayed on the monitor SMON at the repair workstation SST.

In this case, the X-ray images or the electronic images, as well as the printed circuit board layout images are displayed together with solder-joint-specific measured value information which characterizes measured physical parameters of checked defective solder joints, optionally together with statistical information about the frequency of occurrence of defects. The information is displayed alphanumerically and/or symbolically in the X-ray images.

A further program module of the control program is configured in such a way that the solder-joint-specific quality information and/or solder-joint-specific measured value information which characterizes measured physical parameters of checked solder joints, is compared with predefinable production process threshold values and that, depending on the comparison, process control data are formed. For example, the production process threshold value predefined is a specific amount of solder which is to be applied per predefinable solder joint. If, using a comparison of this production process threshold value or production process reference value with the corresponding solder amount measured value information, the result is that this threshold or reference value is overshot or undershot by a predefinable tolerance range, the data processing device C forms alphanumeric and/or graphical information which describes the reference value and/or the measured value information and/or the extent of overshooting or undershooting the reference value. Furthermore, the data processing device may determine that (those) device(s) (L, B, R) which cause(s) the overshooting or undershooting of the amounts of solder. This information is fed to the monitor SMON of the repair workstation SST and to the monitor of that device (e.g. R) which is causing the overshooting or undershooting of the amounts of solder. Appropriate screen displays are illustrated in FIG. 10.

Furthermore, the data processing device C may form an item of control information for this device (e.g. R) which effects a change in the operating parameters of this device. If, for example, the reference value is exceeded to a certain extent, then the control information (that is to say process control data) are formed in such a way that the device R reduces the amount of solder per solder joint appropriately. These procedures, which are carried out for the direct control of the continuous production process, may already be carried out on-line before the occurrence of soldering defects, that is to say at times at which "solder joint defect free" quality information is still being formed.

Screen displays in conjunction with the configuration of measured values and of reference values ("upper warning limit", "lower warning limit") are illustrated in FIGS. 11 to 14.

Using the solder-joint-specific quality information and/or using the solder-joint-specific measured value information, a test is therefore carried out, for solder joints whose physical parameters deviate from the predefinable production process threshold values or reference values, as to which of the first and/or the second and/or the third devices L, B, R this deviation is to be assigned. Depending on this assignment, the first and/or the second and/or the third devices (L, B, R) and, if appropriate, also the associated visual display device (LMON, BMON, RMON) are adjusted using the process control data. The display devices are, in particular, fed with the alphanumeric and/or graphical information that is formed by the data processing device C and which characterizes the reference value and/or the measured value information and/or the extent of the overshooting or undershooting of the reference value.

A further program module is configured in such a way that the solder-joint-specific quality information and/or the solder-joint-specific measured value information which characterizes measured physical parameters of checked solder joints is correlated with grey-value parameters of X-ray images of the solder joints and, on the basis of the correlation, criteria for the formation of the solder-joint-specific quality information and of solder-joint production process threshold values are generated.

That is to say, rules for the formation of the solder-joint-specific quality information and of solder-joint production process threshold values are generated. The starting point is the measured value information from defect-free and defective printed circuit boards, these data being treated statistically, as well as component-specific parameters which are stored in a scaling library.

As already described, the device I measures physical parameters of the solder joints, for example geometric dimensions or the profile of the solder joints. One profile parameter, or preferably several profile parameters, such as two height points on the meniscus, the difference between these height points or between each of the height points and the lowest point on the solder joint surface, or a vertical cross-sectional area of the solder joint is or are selected. These profile parameters of solder joints of particularly good or particularly poor quality are combined or correlated with grey-value parameters of the X-ray images of the corresponding solder joints. As a result, automatically determined profile parameters and limit values are selected, these forming new decision criteria for future assessments of the quality of solder joints.

Within the context of the process according to the invention, therefore, solder-joint-specific measured value information is evaluated on-line and transmitted to different devices in the production process. X-ray defect images are used on-line at the repair workstation. Quality information, specifically, inter alia, measured value information, are assigned to the individual production steps or the corresponding devices and displayed there. As a result of the feedback of this information, the production process is controlled. Furthermore, layout-oriented statistics are generated on-line. Finally, using component-relevant data and statistically treated measured value information, rules relating to the solder-joint type are defined for the detection of soldering defects and process limit values.

What is claimed is:

1. Process for testing solder joints on printed circuit boards,
   the quality of the solder joints being checked for defects by means of X-rays,
   solder-joint-specific quality information being formed,
   X-ray images of the solder joints being generated and the X-ray images and/or images of the graphical layout of the printed circuit boards being displayed on a visual display device (SMON) at a repair workstation (SST),
   the X-ray images and/or images of the graphical layout of the printed circuit boards which have a defective solder joint being displayed on the visual display device (SMON), with a marking of the location of the defective solder joint on the printed circuit board and together with associated defect data.

2. Process according to claim 1, characterized in that the X-ray images and/or the images of the graphical layout of the printed circuit boards are displayed together with solder-joint-specific measured value information which characterizes measured physical parameters of checked defective solder joints, and/or with statistical information about the frequency of occurrence of defects.

3. Process according to one of the preceding claims, characterized in that the defect data are displayed adjacent to the associated solder joints.

4. Process according to claims 1 or 2, characterized in that the information is displayed alphanumerically and/or symbolically in the X-ray images.

5. Circuit arrangement for testing solder joints, comprising
   a device (I) for checking the quality of the solder joints for defects by means of X-rays,
   the device forming solder-joint-specific quality information and generating X-ray images of the solder joints,
   a device (I) for checking the quality of the solder joints for defects by means of X-rays,
   the device forming solder-joint-specific quality information and generating X-ray images of the solder joints,
   a visual display device (SMON) on a repair workstation (SST), the device displaying the X-ray images and/or images of the graphical layout of the printed circuit boards, and
   a controller (CPU) having an associated control program which defines the operation of the repair workstation (SST),
   the control program being configured in such a way that the X-ray images and/or images of the graphical layout of the printed circuit boards which have a defective solder joint are displayed on the visual display device (SMON), with a marking of the location of the defective solder joint on the printed circuit board and together with associated defect data.

6. Circuit arrangement according to claim 5, characterized in that the control program is also configured in such a way that the visual display device (SMON) displays the X-ray images and/or images of the graphical layout of the printed circuit boards together with solder-joint-specific measured value information which characterizes measured physical parameters of checked defective solder joints, and/or that the visual display device (SMON) displays the X-ray images and/or the images of the graphical layout of the printed circuit boards together with statistical information about the frequency of occurrence of defects.

7. Circuit arrangement according to claim 5 or 6, characterized in that the control program is also configured in such a way that the defect data are displayed adjacent to the associated solder joints.

8. Circuit arrangement according to one of claims 5 or 6, characterized in that the control program is also configured in such a way that the visual display device (SMON) displays the information alphanumerically and/or symbolically in the X-ray images.

9. A circuit arrangement according to claim 7, wherein the control program is also configured in such a way that the visual display device displays the information alphanumerically and/or symbolically in the X-ray images.

10. A process according to claim 3, wherein the information is displayed alphanumerically and/or symbolically in the X-ray images.

* * * * *